United States Patent [19]
Lurie et al.

[11] Patent Number: 5,454,779
[45] Date of Patent: Oct. 3, 1995

[54] DEVICES AND METHODS FOR EXTERNAL CHEST COMPRESSION

[75] Inventors: Keith G. Lurie; Todd J. Cohen, both of San Francisco, Calif.

[73] Assignee: The Regents of the University of California, Oakland, Calif.

[21] Appl. No.: 226,431

[22] Filed: Apr. 12, 1994

Related U.S. Application Data

[63] Continuation of Ser. No. 686,542, Apr. 17, 1991, abandoned.
[51] Int. Cl.⁶ .......................... A61H 31/02; A61N 1/00
[52] U.S. Cl. .......................... 601/43; 607/142
[58] Field of Search .......................... 128/639; 607/142, 607/152, 153; 601/41, 43, 44; 2/160, 161 R; 15/227

[56] References Cited

U.S. PATENT DOCUMENTS

| | | | |
|---|---|---|---|
| 517,481 | 4/1894 | Pressey | 128/30.2 |
| 728,003 | 5/1903 | Pfanschmidt et al. | |
| 1,175,671 | 3/1916 | Ackeen | 128/30.2 |
| 1,460,927 | 7/1923 | Thompson et al. | |
| 2,029,951 | 2/1936 | Smith | 15/227 |
| 2,067,268 | 1/1937 | Hans | 128/30.2 |
| 2,069,449 | 2/1937 | Jensen | 15/227 |
| 2,071,365 | 2/1937 | Stroop | 15/227 X |
| 2,204,738 | 6/1940 | Swan | 128/30.2 |
| 2,571,606 | 10/1951 | Peterson | 15/227 |
| 2,742,251 | 4/1956 | Udvardy | |
| 2,879,765 | 3/1959 | Featherston | |
| 3,228,392 | 1/1966 | Speyer | |
| 3,460,182 | 8/1969 | Grande, Jr. | 15/227 |
| 3,534,733 | 10/1970 | Phipps et al. | 128/643 |
| 3,783,865 | 1/1974 | Ricketts | 128/643 |
| 3,958,564 | 5/1976 | Langguth | 128/643 |
| 4,059,099 | 11/1977 | Davis | |
| 4,077,400 | 3/1978 | Harrigan | |
| 4,095,590 | 6/1978 | Harrigan | |
| 4,166,458 | 9/1979 | Harrigan | |
| 4,196,722 | 4/1980 | Vanderwoude | 128/28 |
| 4,198,963 | 4/1980 | Barkalow et al. | 128/802 X |

(List continued on next page.)

FOREIGN PATENT DOCUMENTS

| | | | |
|---|---|---|---|
| 601773 | 3/1926 | France | 15/227 |
| 1476518 | 4/1967 | France | |
| 2382889 | 10/1978 | France | |
| 468358 | 11/1928 | Germany | |
| 188989 | 5/1937 | Switzerland | |
| 201496 | 7/1923 | United Kingdom | 15/227 |
| 274306 | 7/1927 | United Kingdom | |
| 1187274 | 4/1970 | United Kingdom | |
| 8500018 | 1/1985 | WIPO | 128/802 |

OTHER PUBLICATIONS

Wiener Medizinische Wochenschrift, p. 807, Aug. 5, 1939
Brochure in Biomotor Company, Munich, W.G., undated.
Lurie et al. (1990) J. Am. Med. Assoc. Oct. 3, 1990, p. 1661
San Francisco Examiner, "Toilet Plunger Successful in CPR," Oct. 1990.
Adv. Cardiac Life Support, Ch. 4, Am. Heart Assoc. 2. Ed, 1987.
"CPR: The 'P' Stands for Plumber's Helper", Lurie et al. JAMA, Oct. 3, 1990, p. 1661.

Primary Examiner—Mary Beth O. Jones
Attorney, Agent, or Firm—Townsend and Townsend Khourie and Crew

[57] ABSTRACT

A method for performing cardiopulmonary resuscitation employs an applicator device having a body with an upper surface and a lower surface. The lower surface includes provisions for detachably securing to the patient's chest, such as a vacuum cup or an adhesive layer. For manual resuscitation, the upper surface will include a strap or other means for securing a performer's hand thereto. For automatic applications, a mechanical drive member will be secured to the upper surface. By alternately pressing and lifting on the applicator device, the patient's chest can be compressed and expanded to improve induced ventilation and circulation.

35 Claims, 4 Drawing Sheets

U.S. PATENT DOCUMENTS

| | | |
|---|---|---|
| 4,237,872 | 12/1980 | Harrigan . |
| 4,273,114 | 6/1981 | Barkalow et al. . |
| 4,429,688 | 2/1984 | Duffy ................................... 128/28 |
| 4,745,910 | 5/1988 | Day et al. ............................. 128/28 |
| 4,747,397 | 5/1988 | Magovum ............................ 128/67 X |
| 4,852,574 | 8/1989 | Inoue et al. ............................ 128/643 |
| 4,881,527 | 11/1989 | Lerman ................................. 128/30.2 |
| 4,984,987 | 1/1991 | Brault et al. ......................... 128/28 X |
| 5,295,481 | 3/1994 | Geeham ................................... 601/43 |

DEVICES AND METHODS FOR EXTERNAL CHEST COMPRESSION

This is a continuation of application Ser. No. 07/686,542, filed Apr. 17, 1991, now abandoned.

BACKGROUND OF THE INVENTION

1. Field of the Invention

The present invention relates generally to devices and methods for performing external chest compression as a part of cardiopulmonary resuscitation procedures. In particular, the present invention relates to the use of devices which provide for alternately compressing and actively expanding a patient's chest to induce both ventilation and blood circulation.

Sudden cardiac arrest is a major cause of death worldwide and can arise from a variety of circumstances, including heart disease and trauma such as electrical shock and suffocation. To improve a patient's chance of survival (and diminish the likelihood of brain and heart damage resulting from oxygen deprivation), it is essential that measures be taken as soon as possible to at least partially restore the patient's respiration and blood circulation. Approximately thirty years ago, techniques for external chest compression, generally referred to as cardiopulmonary resuscitation (CPR), were developed and have enjoyed great success in reducing mortality resulting from sudden cardiac arrest. Such techniques, however, have remained largely unchanged over the past two decades.

External chest compression relies on actively applying pressure to the patient's chest in order to increase intrathoracic pressure. Such pressure increase will induce blood movement from the region of the heart and lungs through the peripheral arteries, thus partially restoring the patient's circulation. Phase 1 of traditional CPR is referred to as the "active compression phase" where the chest is compressed by the direct application of external pressure. Phase 2, referred to as the "relaxation phase," occurs when pressure is withdrawn and the natural elasticity of the patient's chest wall causes expansion. While such expansion is generally sufficient to refill the cardiac chambers with some blood, it is insufficient to ventilate the patient, i.e., fill the lungs with sufficient air to oxygenate the blood. Thus, conventional CPR further requires periodic ventilation of the patient, e.g., mouth-to-mouth ventilation, in order to provide the air necessary for blood oxygenation.

Manual CPR procedures generally require performers to kneel over the patient and to apply pressure using the palms of their hands to the patient's sternum as the patient lies supine on a flat surface. If no one else is available, the performer must periodically shift position to ventilate the patient through a mouth-to-mouth procedure. Such manual procedures are thus very tiring to the performer and furthermore have been found to result in only limited restoration of respiration and circulation.

Manual CPR procedures can also result in injury to the patient. For example, pressure applied by the palm of the hand can fracture the patient's sternum and/or ribs and cause other traumatic injury, especially if the performer's hand position is inadvertently shifted laterally to an improper location on the patient's chest.

The performance and safety of CPR procedures can be enhanced through the use of various mechanical and automatic machines for applying external chest compression and optionally ventilating the patient by providing supplemental oxygen or air. The machines may be as simple as a "cardiac press" which is a manually operated lever which provides a mechanical advantage in performing chest compression. More sophisticated machines can provide chest compression and/or ventilation through a variety of other mechanisms, including the use of pressurized chambers for compressing the chest cavity. While such machines can be very effective, their bulk, weight, and cost limit their availability. In particular, such machines are not widely available outside of medical facilities and their size is a deterrent to providing such equipment in emergency vehicles.

CPR is often administered in conjunction with other procedures which, taken together, are referred to as advanced cardiac life support (ACLS). Most commonly, CPR is administered while the patient undergoes both electrocardiographic monitoring (ECM) and electrical defibrillation. Both ECM and defibrillation require the attachment of electrodes to the patient's chest. The need to attach electrodes can interfere with the ability to administer CPR, particularly the ability to administer manual CPR. In the case of manual CPR, the performer can also be exposed to electrical shock when current is applied to perform defibrillation.

It would therefore be desirable to provide improved devices and methods for performing external chest compression in conjunction with CPR and ACLS procedures. It would be particularly desirable if such methods and devices provided enhanced ventilation and blood circulation in the patient undergoing treatment, preferably reducing or eliminating the need to separately ventilate the patient. Desirably, the methods and devices should be simple and easily stored so that they can be maintained in emergency vehicles, non-medical facilities, and even the home. The devices should be suitable for performing enhanced manual CPR, in particular by converting Phase 2 chest expansion from a passive event to an active process to improve venous blood return from the heart and enhance airflow into the lungs (facilitated ventilation). The devices should further facilitate the simultaneous performance of electrocardiographic monitoring and/or electrical defibrillation, preferably reducing the performer's exposure to electrical shock from the electrode attachment.

2. Description of the Background Art

U.S. Pat. No. 4,881,527, describes a chamber which may be placed over a patient's chest to alternately apply pressure and vacuum to compress and expand the chest. U.S. Pat. Nos. 4,429,688 and 4,196,722, describe hand-held vacuum cups which are intended for applying percussive therapy to the lungs (chest physiotherapy). The devices are intended for repeatedly striking a patient's chest, not for applying a continuous compression and expansion. A variety of vacuum cup designs have been proposed as body massage devices. See, for example, U.S. Pat. Nos. 2,879,765; 2,742,251; 1,460,927; and 728,003, and British Patent Specification 274,306. German Patentschrift 468358 may also be pertinent.

A device for applying pressure and vacuum to a patient's abdomen to assist in breathing was described by Dr. Rudolf Eisenmenger in Wiener Medizinische Wochenschrift, page 807, Aug. 5, 1939. The device is further described in a brochure of the Biomotor Company, Munich, Germany, undated.

Anecdotal reports of the use of toilet plungers for performing CPR have been made by one of the inventors herein. See, Lurie et al. (1990), *Journal of the American Medical Association,* Oct. 3, 1990, page 1661; and San Francisco Examiner, article entitled "Toilet Plunger Successful in CPR," October 1990.

The use of mechanical devices for performing chest compression and CPR is described in *Textbook of Advanced Cardiac Life Support,* Chapter 4, American Heart Association, Second Edition, 1987.

The full disclosures of each of these references are incorporated herein by reference.

SUMMARY OF THE INVENTION

According to the present invention, devices and methods are provided for the enhanced performance of cardiopulmonary resuscitation (CPR) and advanced cardiac life support (ACLS) procedures. The devices comprise an applicator which facilitates the application of pressure to compress the chest of a patient suffering from cardiac arrest. The applicator is intended to distribute the applied force substantially evenly over a portion of a patient's chest, thus reducing the risk of injury to the patient. The applicator further includes an adherent lower surface which allows active positive expansion of the patient's chest by lifting of the applicator between successive compression strokes. In this way, significant improvement in patient respiration and circulation can be achieved when compared to conventional CPR where the chest is passively, not actively, expanded.

In a particular embodiment of the present invention, the device facilitates the performance of manual CPR where a performer applies pressure directly to an upper surface of the applicator, typically using the open palms of both hands. In such cases, the applicator will comprise an applicator body having upper and lower surfaces, where the upper surface includes means for securing at least one hand thereto. In this particular embodiment, the performer can continuously press and lift on the upper surface without the need to grasp any portion of the applicator. Thus, the performer can carry out CPR using his or her hands in a generally conventional manner, with the additional benefit that the ventilation and blood circulation is enhanced while the risk of injury to the patient is reduced.

The manual applicator of the present invention will usually be in the form of a flexible vacuum cup, where the vacuum or suction provides at least a portion of the adherence and the resilient nature of the cup provides the desired cushion. Optionally, a lower lip of the cup will be coated with an adhesive to further promote adherence. Alternatively, the applicator can be in the form of a resilient pad with an adhesive material or layer present on a lower surface thereof. In the latter case, the pad distributes the applied pressure substantially uniformly over the contact area with the patient's chest while the adhesive surface provides for expansion of the chest as the performer lifts up on the pad. In some cases, it may be desirable to combine the two approaches with an adhesive present on the lower surface of the vacuum cup. In this way, once the applicator is properly positioned on the patient's chest, the physician will shift only minimally if at all. Thus, traumatic sternal and rib injuries resulting from the mislocated application of compression force are reduced.

In a preferred aspect of this embodiment, the manual applicator can further include one or more electrodes present on the lower surface of the applicator body. The electrode will be disposed so that it contacts the patient chest when the applicator is in place and will be useful in performing electrocardiographic or other monitoring procedures and/or electrical defibrillation when connected to appropriate external systems. When the applicator includes such an electrode, it may be desirable to provide a glove or other protective barrier as part of the hand securing means. In this way, the risk of accidental electrical injury to the performer is reduced.

In another particular embodiment of the present invention, an applicator body similar to that described above can be connected to a mechanical drive member. The mechanical drive member can be a simple handle, a powered drive system, or any other mechanical link which is used in place of direct manual manipulation of the applicator as described above. When the applicator is other than for manual use, the applicator body will include an electrode disposed on its lower surface to facilitate electrocardiographic monitoring and/or electrical defibrillation. In the case of manual devices with a handle, it will be particularly useful to include a handle-mounted display which provides patient status and feedback information to the performer.

DESCRIPTION OF THE SPECIFIC EMBODIMENTS

Figure 1:
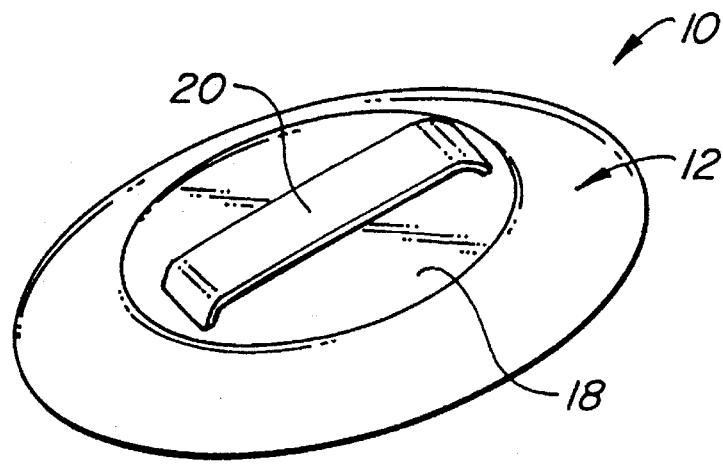
FIG. 1 is a perspective view of an applicator device constructed in accordance with the principles of the present invention.

According to the present invention, methods and devices are provided for performing manual and automated cardiopulmonary resuscitation (CPR), optionally in combination with electrocardiographic monitoring (ECM) and/or electrical defibrillation as part of advanced cardiac life support (ACLS) procedures. The device comprises an applicator body having an upper surface and a lower surface. The lower surface is adapted to adhere to a patient's chest during the performance of CPR so that the intrathoracic region of the chest can be both compressed by pressing on the applicator body and actively expanded by lifting upward on the applicator body.

In a particular embodiment intended for manual CPR, the upper surface of the applicator body will include a strap or other means for securing at least one hand of the person performing the CPR procedure. In this way, the performer can alternately apply active compression and active expansion by pushing and pulling with the strapped hand(s) without the need to grasp the applicator body in any way. This is a great advantage when the CPR is being performed over extended periods since the need to periodically grasp the applicator to expand the patient's chest would be very tiring to the performer. In addition, time wasted in relocating the performer's hands to the proper chest position would be reduced since the applicator would remain secured to the proper location on the chest by vacuum and/or other adhesive means.

In another specific embodiment, the upper surface of the applicator body can be attached to a mechanical drive element, such as a handle or a mechanical link which is part of a powered automatic drive system. In this way, active automatic compression and expansion of the patient's chest can be performed.

In both manual and powered systems, the active expansion of the chest which occurs when the applicator body is lifted causes a negative pressure within the intrathoracic region, drawing air into the lungs to ventilate the patient. This is a particular advantage since it reduces or eliminates the need to otherwise ventilate the patient, such as through mouth-to-mouth resuscitation. In addition, such active expansion causes peripheral blood to move more rapidly back into the right side of the heart and lungs, resulting in increased left heart blood flow during the next compression phase.

Optionally, the applicator body will include an electrode in its lower surface which can facilitate performance of ECM and/or electrical defibrillation.

The applicator body acts as an interface element between a force-applying source, e.g., the performer's hands or the mechanical drive element, and the sternum region on the patient's chest to which the force is applied. The applicator is designed to both uniformly distribute the applied force over a predetermined area, i.e., the contact area between the applicator and the chest, as well as to provide a cushion to decrease the likelihood of injury resulting from the applied compressive force. Usually, the applicator body will be resilient to provide the desired cushion and may further have the ability to distribute the force uniformly by conforming to the contour of the patient's chest. In addition, the applicator is designed to remain fixed to the chest wall at the desired location for applying compression and expansion, thus eliminating the need to relocate the proper location each time compression is resumed, as is necessary with traditional CPR.

A variety of specific designs for the applicator body can fulfill these objectives. The applicator body can be formed as a solid pad from a resilient material, such as a natural or synthetic elastomer. Alternatively, the applicator body may be formed as an open or partially open structure, optionally containing an enclosed gas, gel, or the like, to enhance the shock absorbing and distributing capability of the body. In the case of pad-like applicator bodies, it will be necessary to provide additional means for adhering the lower surface of the body to the patient's chest. Typically, an adhesive material can be formed over all or part of the lower surface.

Suitable adhesive materials include pressure-sensitive adhesives such as those which are commonly used on medical bandages, transdermal patches, and other medical applications. The most useful adhesives will be natural and synthetic rubber based formulations, particularly polyisobutylenes. Other suitable adhesives include acrylic and silicon-base materials. When used in conjunction with electrodes, as described hereinafter, swollen hydrogels, such as poly(vinyl pyrrolidone), may find use.

The preferred embodiment of the applicator body will comprise a resilient vacuum cup having a hollow interior, where the hollow interior is placed against the patients chest so that a vacuum or "suction" is created when the applicator body is compressed thereagainst. Thus, when the vacuum cup structure is subsequently lifted according to the method of the present invention, the patient's chest will be actively expanded. The vacuum cup design is advantageous both because of its inherent adherent characteristics as well as its natural resilience which provides a cushion to protect the patient and promote the even distribution of pressure (force) over the interface region with the patient's chest. Even with the vacuum cup design, it will frequently be desirable to provide an adhesive layer (using the materials described above) over at least a portion of the lip of the vacuum cup which contacts the patient's chest. Adhesive helps hold the vacuum cup applicator body in place and helps assure that the desired vacuum is maintained.

It will frequently be desirable to form the applicator body as a laminated or layered structure, usually having one or more upper layers which are rigid relative to the lower layer(s). The relatively rigid upper layer(s) will act to receive a localized compressive force, either from the performer's hand or from a mechanical driver, and to evenly distribute the force over the lower, more resilient layers. The ability to distribute the force over the resilient lower layers is particularly important with solid applicator body structures which are subject to localized compression, possibly causing a "punch-through" effect.

For manual applicator designs, means for securing at least one hand will be provided on the upper surface of the applicator body. The means for securing can be a strap, mitten, glove, or the like, which permits the performer to both press down on the applicator body and lift upward on the body without the need to grasp the applicator body in any way. The securing means should be attached to the upper surface so that the upward force applied by the performer's hand will be relatively evenly distributed over the applicator body. The use of a relatively rigid upper surface on the applicator body will help provide such even force distribution.

The dimensions of the applicator body will be chosen to provide a desired interface area between the applicator and the patient's chest. Typically, for adult patients, the applicator will have a circular periphery with a diameter in the range from about 8 to 25 cm, preferably being in the range from about 10 to 20 cm. For children, the dimensions may be as small as 3 cm. Other, non-circular geometries may also find use, and it is necessary only that the applicator body be shaped to provide for a desired force distribution over the patient's sternum as well as to provide for sufficient adherence to allow the patient's chest to be expanded when the applicator body is raised upward.

The thickness of the applicator body is not critical and will depend on the particular body design. For solid, pad-like applicator bodies, the thickness will typically be in the range from about 1 to 10 cm, more typically in the range from about 2 to 8 cm, depending on the resiliency of the material employed. For vacuum cup designs, the maximum thickness, i.e., the maximum air gap, will be in the range from about 1 to 15 cm, more usually from about 5 to 12 cm. For manual applications, it will be desirable to provide a flat upper surface so that the user can press down evenly over the surface with one or both hands in a manner similar to conventional CPR. In this way, the performer will experience the same "feel" as conventional CPR with the advantages of the present invention of patient protection and improved ventilation and circulation. In some cases, it may be desirable to shape the lower surface of the applicator body to conform to the general contours of the human chest. In addition, it may be desirable to provide a plurality of sizes of the applicator in a single kit so that a particular applicator may be selected for the individual patient. Such kits would have applicators as small as about 3 cm in diameter for children to as large as 25 cm, usually 20 cm, in diameter for adults.

It will frequently be desirable to provide one or more electrodes in the lower surface of the applicator body. The electrodes will be exposed on the surface so that they will contact the patients chest when the applicator body is in use. The electrode will be internally connected to an electrical connector or plug, typically located on the side of upper surface of the applicator body. The connector or plug will be selected to allow interconnection with conventional ECM and/or electrical defibrillation equipment. Combination ECM/defibrillation equipment is commercially available from suppliers such as Hewlett-Packard Co., Palo Alto, Calif., and Physio Control, Seattle, Wash. When used with such systems, the applicator of the present invention can act as one of the two (or more) "paddle" connectors which are secured to the patient's chest for monitoring and/or defibrillation.

Figure 2:
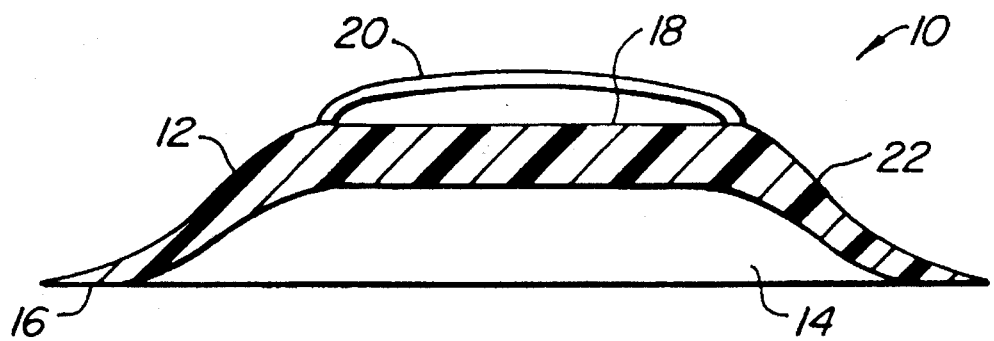
FIG. 2 is a cross-sectional view of the applicator device of FIG. 1.

Referring now to FIGS. 1 and 2, a first embodiment of the applicator device of the present invention, intended for manual CPR, is illustrated. The device 10 comprises a vacuum cup body 12 having a concave interior 14 which opens into a lower surface defined by a peripheral lip 16. The vacuum cup 12 has a substantially flat upper surface 18 having a strap 20 extending thereacross. The strap 20 is firmly secured to the upper surface so that a user can place one or both hands beneath the strap with the hand(s) being open to press directly against the upper surface.

The vacuum cup body 12 is relatively thick across its flat upper surface and tapers down to form a skirt 22 terminating at the periphery of lip 16. The thick upper surface region provides sufficient rigidity so that the applicator body 12 will not involute or "cave in" as the user presses against the upper surface. Instead, the lip 16 and skirt 22 will tend to spread outward reducing the volume of air in the concave interior 14 and providing the desired vacuum. The vacuum cup 12 will transmit sufficient force to compress the patient's chest by a desired amount, typically 3.5 to 5 cm. After the desired compression of the chest is completed, the user will lift on the applicator body 12 by raising one or both hands which in turn lift through the strap 20. The reduced pressure within the concave interior 14 will cause a vacuum or suction which acts to raise the patient's chest and actively expand the intrathoracic cavity.

Using the device 10, the performer is able to perform CPR in a manner similar to conventional manual CPR, with reduced exposure to injury since the application of force is localized to the intended region on the patient's chest with the position being "anchored" by the device itself. Additionally, the ability to actively raise the patient's chest and expand the intrathoracic cavity provides for improved ventilation and circulation of the patient.

Figure 3:
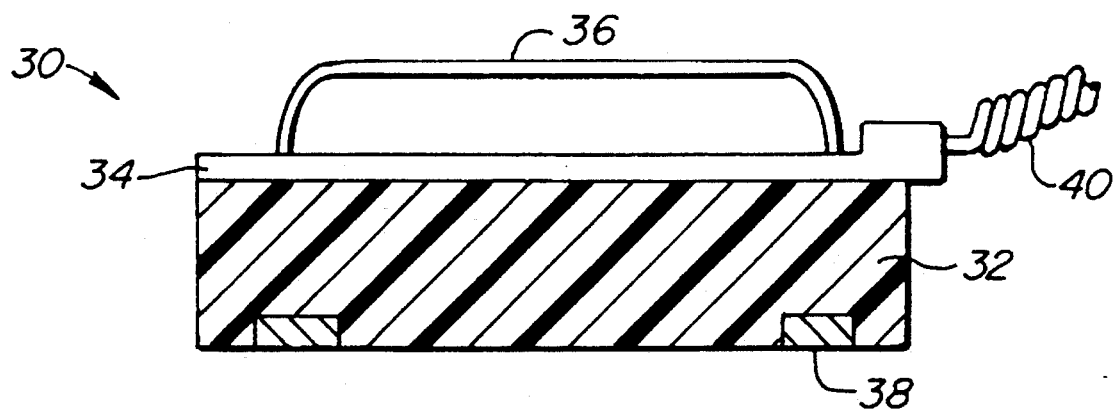
FIG. 3 is a cross-sectional view of a first alternate embodiment of an applicator device constructed in accordance with the principles of the present invention.

Referring now to FIG. 3, an alternate embodiment of a manual applicator device 30 constructed in accordance with the principles of the present invention is illustrated. The device 30 comprises a solid resilient pad structure 32 laminated to a relatively rigid upper plate 34. The resilient pad 32 can be formed from a wide variety of natural and synthetic polymers having sufficient resiliency to conform to the contours of the patient's chest while retaining sufficient compressive strength to permit the transmission of the desired force to the chest. Suitable polymers include neoprenes, low density polyethylene, soft polyvinylchloride (PVC) compounds, natural rubbers, synthetic rubbers, and the like. Suitable polymeric structure include open cell and closed cell foams. The solid pad may also comprise fluid-filled bags and structures, such as gel-filled bags and air-filled structures, which can transmit the desired force while providing desired resilience and conformity.

The upper plate 34 will be rigid relative to the resilient pad 32, typically being a rigid plastic material. A strap 36 is secured to the upper plate 34 and allows the user to place one or both hands therein in a manner similar to that described for device 10.

Applicator 30 further includes an electrode 38 which is in the form of a ring extending about the periphery of the lower surface of the pad 32. The electrode 38 will be formed from a suitable material, such as electrically conductive metals, and will be interconnected with an electrical connector cord 40 which is suitable for interconnection with an ECM system, an electrical defibrillator, or a combination ECM/defibrillator unit. Such electrode applicators will frequently be used in combination with an electrically-conductive gel, such as those commonly used with defibrillator electrodes, which can further enhance the adhesive characteristics of the applicator.

To provide the necessary adherence, the lower surface of pad 32 is covered with an adhesive which is suitable for detachably adhering to the patients chest. Suitable adhesives are described above.

Figure 4:
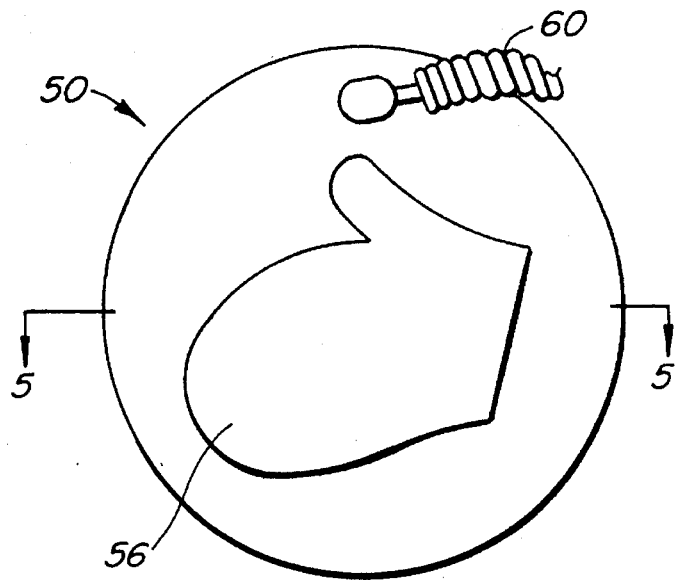
FIG. 4 is a top plan view of a second alternate embodiment of an applicator device constructed in accordance with the principles of the present invention.
Figure 5:
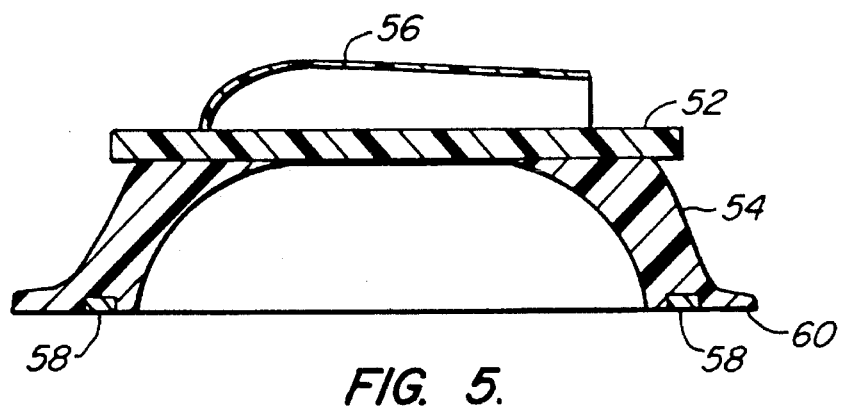
FIG. 5 is a cross-sectional view taken along line 5—5 of FIG. 4.

A second alternate embodiment 50 of the applicator device of the present invention is illustrated in FIGS. 4 and 5. The applicator device 50 includes a relatively rigid upper plate 52 and a depending vacuum cup structure 54 formed from a relatively resilient material, i.e., a material which is able to spring back. A mitten 54 is secured to the upper surface of plate 52 and is shaped to receive a performer's hand. An electrode 58 is disposed in the lip 60 of the vacuum cup 54. The electrode is interconnected to a cord 60 intended for hook-up to conventional ECM and/or defibrillation equipment.

The device 50 combines certain of the advantages of each of the previous embodiments. The use of the rigid upper plate 52 helps assure the even application of force to the patient's chest. Use of the vacuum cup structure 54 provides for an entrapped cushion of air in its concave interior, further assuring substantially uniform distribution of pressure to the patient's chest. Finally, the use of the mitten 56, rather than a strap that has previously been described, helps isolate the performer's hand from the other electrodes being used for ECM and/or defibrillation.

Figure 5A:
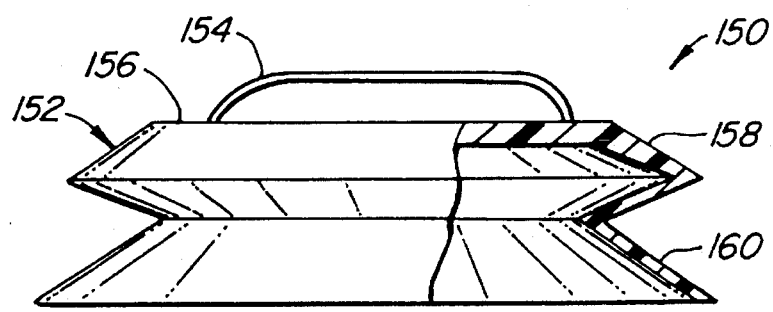
FIG. 5A is a side view of a third alternate embodiment of an applicator constructed in accordance with the principles of the present invention.

FIG. 5A illustrates an applicator 150 having a bellows or accordian configuration. In particular, applicator 150 comprises an applicator body 152 having a handle 154 secured on an upper surface 156. The applicator body 152 includes an upper pleated section 158 and a lower skirt section 160 which together define the desired bellows construction. It will be appreciated that the bellows structure may include additional pleated sections, although usually the structure illustrated will be sufficient. The applicator body 156 will usually be composed of a resilient elastic material, such as a natural rubber or synthetic rubber, and may be formed by conventional molding techniques. The applicator body 156 provides a vacuum cup which permits significant air intrusion or leakage to take place before the desired vacuum is lost.

Figure 6:
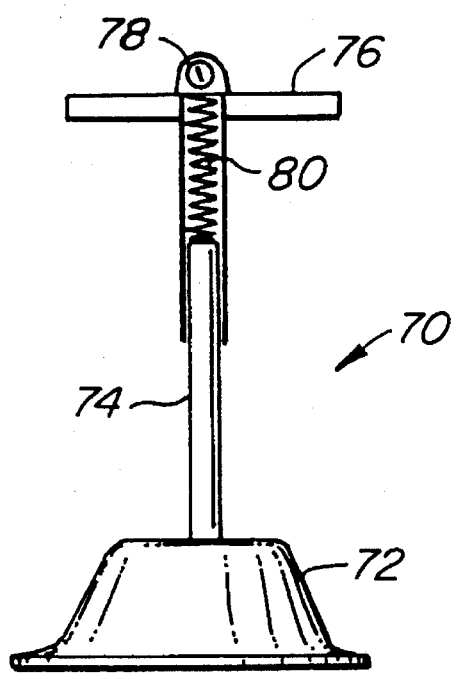
FIG. 6 is an elevational view, with portions broken away, of a third alternate embodiment of the applicator device of the present invention.

An applicator device 70 comprising an applicator body 72 and a handle 74 attached to the upper surface of the applicator body 72 is illustrated in FIG. 6. The applicator body 72 is illustrated as a vacuum cup, similar to that illustrated in FIGS. 1 and 2, but could be any of the other applicator body structures described herein. The use of an elongate handle 74 with the applicator body 72 is desirable for patient's lying on the floor or ground. A T-bar 76 on the handle 74 allows the performer to stand over the patient with one leg straddled on each side of the patient's chest, applying successive downward and upward strokes to compress and actively expand the chest.

Use of the handle interferes with the performer's ability to feel and regulate the pressure and compression being applied to the chest. For that reason, it is desirable to provide feedback information, such as a pressure gauge 78, on the handled device 70. As illustrated, the pressure gauge employs a spring 80 which is disposed between the T-bar 76 and the fixed portion of handle 74. The spring 80 also acts as a shock-absorber which helps limit excessive force applied to the patient. Other pressure measuring devices and transducers would also be suitable.

In embodiments with a handle, it may be desirable to provide a more advanced monitoring panel or readout on the handle (not illustrated) which can display a variety of patient status information and/or feedback to the person performing the CPR. Patient status information includes minute ventilation, temperature, blood pressure, heart rate, respiratory rate, and other vital signs. Such status information will often require separate monitoring devices (not illustrated) attached to the patient, and the display on the handle makes the information immediately available to the person performing the CPR. Feedback information includes pressure or force applied to the patient, depth of compression, compression rate (i.e., cycles per minute), duty cycle (i.e., portion of each cycle in which the patient is compressed), and the like. Such feedback information can be provided as discrete values, e.g., with gauges or digital readouts, or may be provided with a light or sound system which indicates when certain threshold values have been met or exceeded. It may be further desirable to provide a pacing signal, e.g., either a sound or flashing light, to facilitate maintaining a desired compression rate.

Figure 7:
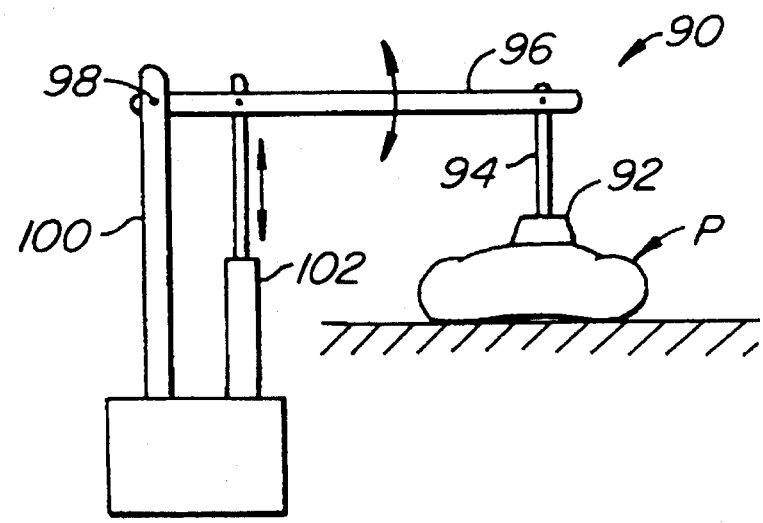
FIG. 7 is a schematic illustration of an applicator device constructed in accordance with the principles of the present invention employed in a powered actuation system.

The applicator device of the present invention may also be employed in a powered system 90 as illustrated schematically in FIG. 7. Applicator body 92 is secured to a vertical drive element 94 which is attached to a reciprocating lever arm 96. The lever arm 96 may be driven in a wide variety of ways. As illustrated, a fixed fulcrum point 98 is provided by post 100 and the lever is reciprocated up and down by a piston and cylinder 102 to provide the desired compression and expansion of the chest.

The applicator 92 is again illustrated as a vacuum cup structure, similar to that illustrated in FIGS. 1 and 2. The applicator 92 could employ any of the other applicator body structures illustrated herein, and will be particularly useful with those structures which include integral electrodes which permit ECM and defibrillation.

Figure 9:
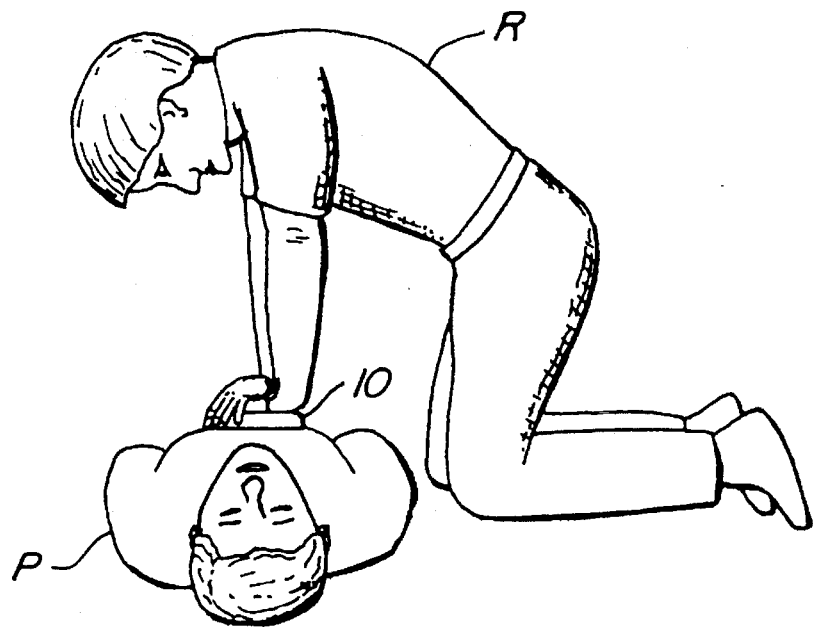
FIG. 9 illustrated the proper placement of the applicator on a patient for resuscitation as illustrated in FIG. 8.
Figure 8:
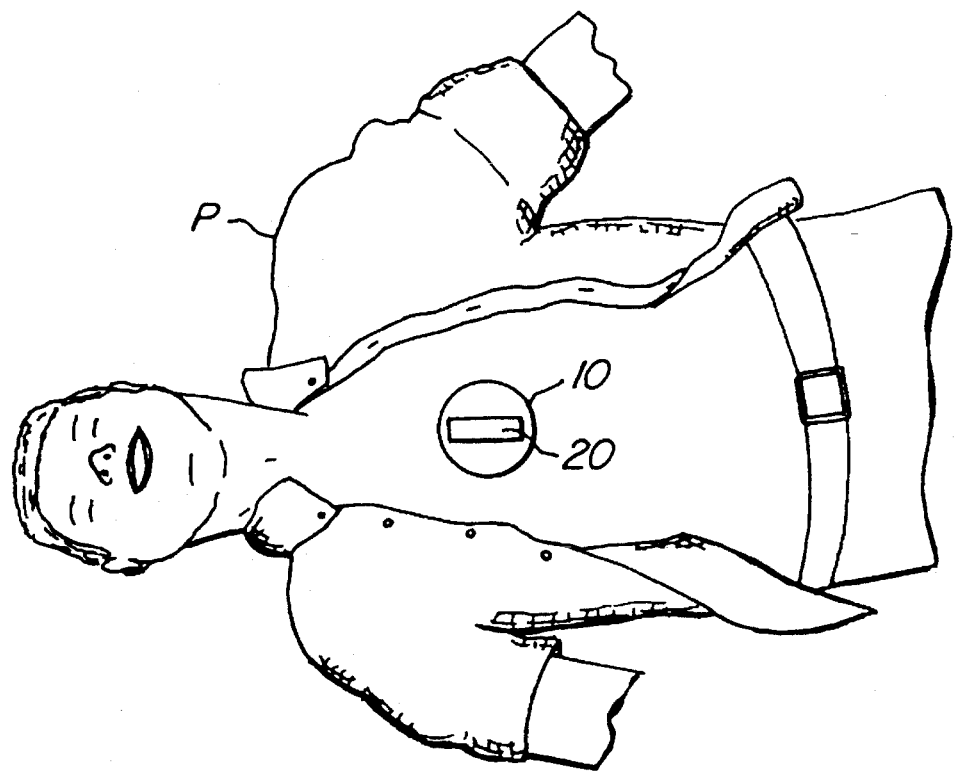
FIG. 8 illustrates the applicator device of FIG. 1 being used to perform manual cardiopulmonary resuscitation.

Referring now to FIGS. 8 and 9, a method according to the present invention for applying manual CPR using the applicator device 10 is illustrated. A patient P suffering from cardiac arrest and apnea is laid on his back on a flat surface and the shirt and collar loosened to provide access to the chest. After the patient's airway is cleared and the chin lifted to tilt the head, the device 10 is placed over the lower portion of the patient's sternum in the region where conventional CPR is applied (FIG. 9).

The performer then places one or both hands under the strap 20 of device 10 and begins external chest compressions at a rate of from 80 to 100 per minute. Optionally, the performer will periodically apply mouth-to-mouth resuscitation or other ventilation in order to ventilate the patient. It is an advantage of the present method, however, that the number of ventilations which must be performed is reduced.

Each chest compression should achieve a compression in the range from about 3.5 to 5 cm, and will be followed by a positive lifting on the chest by the performer by lifting on the applicator device 10. The chest will be lifted and allowed to remain ventilated until the next compression step. Typically, the compression portion of the cycle will last from about 0.2 to 0.7 seconds, while the expansion portion of the cycle will last from about 0.2 to 0.7 seconds, with the compression and expansion portions usually being equal.

The method, as described above, will be continued until heartbeat and respiration are restored or until medical support arrives.

Although the foregoing invention has been described in detail for purposes of clarity of understanding, it will be obvious that certain modifications may be practiced within the scope of the appended claims.

What is claimed is:

1. A method for performing cardiopulmonary resuscitation of a patient suffering cardiac arrest and apnea, said method comprising:

pressing an applicator body against the patient's sternum to compress the patient's chest, wherein sufficient pressure is applied to the sternum to compress the chest in the range from about 3.5 to 5 cm;

lifting the applicator to actively expand the patient's chest wherein a lower surface of the applicator adheres to the patient's chest; and alternating the pressing and lifting steps at a rate in the range from about 80 to 100 repititions per minute until the patient's heartbeat and respiration are restored.

2. A method as in claim 1, wherein at least one of the performer's hands presses directly against an upper surface of the applicator.

3. A method as in claim 1, wherein the lower surface adheres to the patient's chest at a location over the sternum at least in part as a result of suction.

4. A method as in claim 1, wherein the lower surface adheres to the patient's chest at least in part as a result of an adhesive.

5. A method as in claim 6, wherein the patient is lying on a flat surface, a performer kneels next to the patient, and the performer alternately presses and lifts the applicator using fully extended arms.

6. A method as in claim 1, wherein the performer presses against and lifts upon a handle which is secured to an upper surface of the applicator.

7. A method as in claim 6, wherein the applicator is a flexible cup and the performer grasps lateral extensions disposed symmetrically on the handle with each hand, wherein the handle is disposed at the center of the upper surface.

8. A method for performing cardiopulmonary resuscitation of a patient suffering cardiac arrest and apnea, said method comprising:

compressing the patient's chest by manually pressing on an upper surface of a flexible cup having a hollow interior, where a lower lip of the cup is disposed against the patient's sternum resulting in a vacuum, wherein the chest is compressed sufficiently to induce blood circulation from the chest;

actively expanding the patient's chest by manually lifting on the upper surface of the flexible cup, wherein the chest is raised by the vacuum to further induce blood circulation and ventilation; and alternating the compressing and expanding steps according to a preselected rhythm, wherein each compressing step is followed by the expanding step.

9. A method as in claim 8, further comprising securing a performer's hand to the upper surface of the flexible cup prior to compressing and expanding.

10. A method as in claim 9, wherein the performer's hand is secured by a strap attached to the upper surface.

11. A method as in claim 9, wherein the performer's hand is secured by a glove or mitten attached to the upper surface.

12. A method as in claim 8, wherein the patient is lying on a flat surface, a performer kneels next to the patient, and the performer alternately presses and lifts on the upper surface of the flexible cup using fully extended arms.

13. A method as in claim 8, wherein the applicator includes a handle having lateral extensions disposed symmetrically thereon, where the performer grasps the lateral extension with each hand to apply pressure uniformly on the upper surface of the applicator.

14. A method as in claim 8, wherein the patient's chest is compressed in the range from about 3.5 cm to 5 cm at a rhythm in the range from 80 to 100 repititions per minute.

15. A method for performing cardiopulmonary resuscitation of a patient suffering cardiac arrest and apnea, said method comprising:

compressing the patient's chest by manually pressing on an upper surface of a flexible cup having a hollow interior, where a lower lip of the cup is disposed against the patient's sternum resulting in a vacuum, wherein the chest is compressed sufficiently to induce blood circulation from the chest;

actively expanding the patient's chest by manually lifting on the upper surface of the flexible cup, whereby the chest is raised by the vacuum to further induce blood circulation and ventilation;

alternating the compressing and expanding steps according to a preselected rhythm, wherein the chest is lifted and allowed to remain ventilated until the following compressing step; and monitoring the patient's electrocardiographic characteristics using an electrode which is on the lip of the cup.

16. A method for performing cardiopulmonary resuscitation of a patient suffering cardiac arrest and apnea, said method comprising:

compressing the patient's chest by manually pressing on an upper surface of a flexible cup having a hollow interior, where a lower lip of the cup is disposed against the patient's sternum resulting in a vacuum, wherein the chest is compressed sufficiently to induce blood circulation from the chest;

actively expanding the patient's chest by manually lifting on the upper surface of the flexible cup, whereby the chest is raised by the vacuum to further induce blood circulation and ventilation;

alternating the compressing and expanding steps according to a preselected rhythm, wherein the chest is lifted and allowed to remain ventilated until the following compressing step; and defibrillating the patient by applying electrical energy using an electrode which is on the lip of the cup.

17. A method for simultaneously resuscitating and monitoring electrocardiographic activity of a patient suffering cardiac arrest, said method comprising:

pressing an applicator body against the patient's chest at a location over the sternum to compress the chest;

lifting the applicator to actively expand the patient's chest, wherein a lower surface of the applicator adheres to the chest at said location over the sternum;

detecting the patient's electrocardiographic pattern through an electrode in the lower surface of the applicator; and alternating the pressing and lifting steps so that each pressing step will last in the range from about 0.2 to 0.7 seconds and each lifting step will last in the range from about 0.2 to 0.7 seconds until the patient's heartbeat and respiration are restored.

18. A method as in claim 17, wherein a performer manually presses and lifts an upper surface of the applicator body.

19. A method as in claim 18, wherein at least one of the performer's hands is secured to the upper surface.

20. A method as in claim 18, wherein a performer manually presses and lifts the applicator body using a handle attached to an upper surface thereof.

21. A method as in claim 17, wherein the applicator is pressed and lifted using a mechanical reciprocator.

22. A method as in claim 21, wherein the mechanical reciprocator is powered.

23. A method as in claim 17, wherein the electrode is interconnected through a connector on the applicator to an electrocardiogram monitor to produce the electrocardiograph pattern through said electrode.

24. A method for simultaneously resuscitating and defibrillating a patient suffering cardiac arrest, said method comprising:

pressing an applicator body against the patient's chest at a location over the sternum to compress the chest;

lifting the applicator to actively expand the patient's chest, wherein a lower surface of the applicator adheres to the chest at said location over the sternum;

applying a current to the patient's chest through an electrode in the lower surface to effect defibrillation; and alternating the pressing and lifting steps so that each pressing step will last in the range from about 0.2 to 0.7 seconds and each lifting step will last in the range from about 0.2 to 0.7 seconds until the patient's heartbeat and respiration are restored.

25. A method as in claim 24, wherein a performer manually presses and lifts an upper surface of the applicator body.

26. A method as in claim 25, wherein at least one of the performer's hands is secured to the upper surface.

27. A method as in claim 25, wherein a performer manually presses and lifts the applicator body using a handle attached to an upper surface thereof.

28. A method as in claim 24, wherein the applicator is pressed and lifted using a mechanical reciprocator.

29. A method as in claim 28, wherein the mechanical reciprocator is powered.

30. A method as in claim 24, wherein the electrode is interconnected through a connector on the applicator to electrical defibrillation equipment to pass an electric current through said electrode.

31. A method for performing cardiopulmonary resuscitation of a patient suffering cardiac arrest and apnea, said method comprising:

pressing an applicator body against the patient's sternum to compress the patient's chest, wherein sufficient pressure is applied to the sternum to compress the chest in the range from about 3.5 to 5 cm;

lifting the applicator to actively expand the patient's chest wherein a lower surface of the applicator adheres to the patient's chest, the lower surface having a circular periphery with a diameter in the range from about 3 to 20 cm; and alternating the pressing and lifting steps at a rate in the range from about 80 to 100 repetitions per minute until the patient's heartbeat and respiration are restored.

32. A method for performing cardiopulmonary resuscitation of a patient suffering cardiac arrest and apnea, said method comprising:

compressing the patient's chest sufficiently to induce blood circulation from the chest by manually pressing on a relatively rigid portion of an upper surface of a flexible cup having a hollow interior and a relatively resilient circular lower lip with a diameter in the range from about 3 to 20 cm, which lower lip is disposed against the patient's sternum resulting in a vacuum within the cup;

actively expanding the patient's chest by manually lifting on the upper surface of the flexible cup, whereby the chest is raised by the vacuum to further induce blood circulation and ventilation; and alternating the compressing and expanding steps according to a preselected rhythm.

33. A method for performing cardiopulmonary resuscitation of a patient suffering cardiac arrest and apnea, said method comprising:

pressing an applicator body against the patient's sternum to compress the patient's chest, wherein sufficient pressure is applied to the sternum to compress the chest in the range from about 3.5 to 5 cm;

lifting the applicator to actively expand the patient's chest wherein a lower surface of the applicator adheres to the patient's chest; and alternating the pressing and lifting steps at a rate in the range from about 80 to 100 repetitions per minute until the patient's heartbeat and respiration are restored;

wherein the patient is lying on a flat surface, a performer kneels next to the patient, and the performer alternately presses and lifts and applicator using fully extended arms.

34. A method for performing cardiopulmonary resuscitation of a patient suffering cardiac arrest and apnea, said method comprising:

pressing an applicator body against the patient's sternum to compress the patient's chest, wherein sufficient pressure is applied to the sternum to compress the chest in the range from about 3.5 to 5 cm;

lifting the applicator to actively expand the patient's chest wherein a lower surface of the applicator adheres to the patient's chest; and alternating the pressing and lifting steps at a rate in the range from about 80 to 100 repetitions per minute until the patient's heartbeat and respiration are restored;

wherein the performer presses against and lifts upon a handle which is secured to an upper surface of the applicator.

35. A method as in claim 34, wherein the applicator is a flexible cup and the performer grasps lateral extensions disposed symmetrically on the handle with each hand, wherein the handle is disposed at the center of the upper surface.

* * * * *